(12) United States Patent
Unger et al.

(10) Patent No.: US 6,261,217 B1
(45) Date of Patent: Jul. 17, 2001

(54) SEPARATION SET HAVING PLATE-LIKE SEPARATION CONTAINER WITH ANNULAR PINCH VALVE FOR BLOOD COMPONENT PREPARATION

(75) Inventors: Peter Unger, Stockholm; Eric Westberg, Lindingö, both of (SE)

(73) Assignee: Sanguistech Aktiebolag, Karlskoga (SE)

( * ) Notice: Subject to any disclaimer, the term of this patent is extended or adjusted under 35 U.S.C. 154(b) by 0 days.

(21) Appl. No.: 09/403,015

(22) PCT Filed: Apr. 14, 1998

(86) PCT No.: PCT/SE98/00673

§ 371 Date: Oct. 18, 1999

§ 102(e) Date: Oct. 18, 1999

(87) PCT Pub. No.: WO98/46362

PCT Pub. Date: Oct. 22, 1998

(30) Foreign Application Priority Data

Apr. 16, 1997 (SE) .................................................. 9701423

(51) Int. Cl.[7] ......................................................... B04B 7/08
(52) U.S. Cl. ................................ 494/45; 494/23; 494/38; 494/47
(58) Field of Search ................................. 494/18, 23–30, 494/38, 41, 43, 45, 47, 48, 50, 56; 210/781, 782

(56) References Cited

U.S. PATENT DOCUMENTS

| 3,096,283 | * | 7/1963 | Hein . |
| 3,239,136 | * | 3/1966 | Hein . |
| 3,244,362 | * | 4/1966 | Hein . |
| 3,326,458 | * | 6/1967 | Meryman et al. . |
| 3,456,875 | * | 7/1969 | Hein . |
| 3,679,128 | * | 7/1972 | Unger et al. . |
| 3,708,110 | * | 1/1973 | Unger et al. . |
| 3,724,747 | * | 4/1973 | Unger et al. . |
| 3,737,096 | * | 6/1973 | Jones et al. . |
| 3,987,961 |   | 10/1976 | Sinn et al. . |
| 4,111,355 | * | 9/1978 | Ishimaru . |
| 4,142,670 | * | 3/1979 | Ishimaru et al. . |
| 4,304,357 | * | 12/1981 | Schoendorfer . |
| 4,530,691 | * | 7/1985 | Brown ..................................... 494/45 |
| 4,990,132 |   | 2/1991 | Unger et al. . |
| 5,114,396 |   | 5/1992 | Unger et al. . |
| 5,316,540 | * | 5/1994 | McMannis et al. .................... 494/45 |
| 5,651,766 | * | 7/1997 | Kingsley et al. .......................... 604/6 |
| 5,733,253 | * | 3/1998 | Headley et al. ........................ 494/26 |

FOREIGN PATENT DOCUMENTS

| 578086 | * | 1/1994 | (EP) ...................................... 494/45 |
| 85/02561 | * | 6/1985 | (WO) ...................................... 494/45 |
| 87/06857 |   | 11/1987 | (WO) . |
| 96/29081 |   | 9/1996 | (WO) . |

* cited by examiner

*Primary Examiner*—Charles E. Cooley
(74) *Attorney, Agent, or Firm*—Jacobson Holman PLLC

(57) ABSTRACT

A separation set for blood component preparation and similar separations for use in a centrifuge rotor, the set including a plate-like separation container made of a flexible material, an annular pinch valve which is mounted on and divides the separation container into a central section and an annular outer section, a first component container which is connected to the center of the separation container, a second component container which is connected to the circumference of the separation container, and a blood withdrawal tube for supplying blood to the outer section. The blood is separated in the outer section into plasma, buffy coat and red blood cells. Then the plasma is displaced to the first component container and the buffy coat to the central section where it is enclosed through the action of the pinch valve. The separation set with the pinch valve is then removed from the centrifuge and the red blood cells are transferred to the second component container.

20 Claims, 4 Drawing Sheets

SEPARATION SET HAVING PLATE-LIKE SEPARATION CONTAINER WITH ANNULAR PINCH VALVE FOR BLOOD COMPONENT PREPARATION

BACKGROUND OF THE INVENTION

1. Field of the Invention

The invention relates to a separation set for blood component preparation and similar separations in a centrifuge rotor of a type comprising an annular separation compartment and a central compartment, which are arranged concentrically with the axis of rotation of the rotor and communicate with each other via an annular slot, and comprising means for reducing in operation the volume of the separation compartment. The separation set comprises a plate-like separation container of a flexible material and a first component container which by means of a tube is connected to the center of the separation container.

2. Description of the Related Art

In blood component preparation, blood is separated into the components plasma, buffy coat and red blood cells by centrifugation. A sterile set of interconnected flexible containers is used. The presently most common mode of operation is to use a sterile set of interconnected rectangular blood bags, one bag constituting the separation container, to which the blood is supplied, and the others being component containers, to which the separated components are then transferred. The entire set is centrifuged standing in swing-out centrifuge cups and, after centrifugation, the blood components form layers in the separation container according to the increasing specific weight, viz. a plasma layer, a buffy coat layer and a layer of red blood cells. Then the set of bags is removed from the centrifuge and moved to a pressing device for pressing out the plasma layer and then the buffy coat layer to associated component containers. The manual handling of the bags when the layers are in contact with each other results in a certain remixing, and it is inevitable that a certain amount of buffy coat remains in the separation container together with the red blood cells after the pressing-out operation.

Modem blood component therapy, however, requires very pure fractions of plasma and red blood cells, i.e. they should as little as possible be contaminated by the intermediate buffy coat fraction. The pressing-out of the various fractions from the separation container constitutes a critical operation with respect to the achieving of pure components.

An improvement in this respect is disclosed in WO 96/29081, where a more complete pressing-out of the buffy coat fraction is achieved by applying a pulsating pressure to the top of the container.

A different technique of achieving high purity of the separated fractions is to use a centrifuge rotor of the type mentioned by way of introduction, in which an annular separation container is compressed in the separation compartment of the rotor during rotation, and the separated layers are pressed to the central compartment of the rotor while they are affected by the prevailing G field. According to WO 87/06857, a centrifuge rotor of this type is known, and in one embodiment there is described an annular pinch means which acts in the slot-like zone between the annular separation compartment and the central compartment arranged inwardly thereof. A flexible plate-like separation container extending over the separation compartment and central compartment is divided by said pinch means into an outer annular container and an inner central container. A charge of blood is transferred to the annular part and separated by centrifugation. At a certain predetermined rotational speed, the pinch means opens the slot-like connection and at the same time the volume of the annular separation compartment decreases, whereby plasma is displaced via the central part and further on to a centrally connected plasma container, and buffy coat is displaced into the central part. Then the pinch means closes the connection. Plasma is now available in the connected plasma container, buffy coat in the central part of the separation container and red blood cells in the outer part of the separation container. The buffy coat and the red cells must, however, somehow be taken care of before the separation container can be removed from the centrifuge since the action of the pinch means ceases when the cover of the rotor is opened. This problem has not been satisfactorily solved, and therefore this centrifuge variant with the annular pinch means has not been used in practice, although it offers a very advantageous way of displacing a component layer to another container.

SUMMARY OF THE INVENTION

An object of the present invention is to provide a set of containers which solves the above-mentioned problems and permits effective preparation of blood components of high purity by using a plate-like separation container in a centrifuge of the type mentioned by way of introduction. The set of containers according to the invention thus comprises a plate-like separation container of a flexible material and a first component container which by means of a tube is connected to the center of the separation container. The separation set is characterized by an annular pinch valve which is mounted on the separation container and arranged to divide this into a central section and an annular outer section, and a second component container which by means of a tube is connected to said outer section.

The annular pinch means thus follows the container set during its handling in and outside the centrifuge. The transfer of the red blood cells to the second component container is carried out outside the centrifuge after the separation has been completed and the centrifuge can be utilized effectively. In this type of centrifuge, only one charge of blood can be processed in each centrifugation, which means that a short process time in the centrifuge is very important in routine preparation of blood components. The pinch valve can be reused and applied to a new separation container after transfer of the red blood cells to a component container.

The invention is further characterized in that the components plasma and red blood cells will be extremely pure by the buffy coat layer being affected to a very small extent and being mixed to a minimum extent with the neighboring layers during the displacement to the central section of the separation container. The buffy coat layer is displaced radially inwards to the center of the rotor uniformly from all directions and needs not be pressed through a limited outlet opening. Besides the displacement takes place during rotation while the layers are acted upon by the centrifugal force.

Two different embodiments of the invention will now be described in more detail with reference to the accompanying Figures.

DETAILED DESCRIPTION OF THE PREFERRED EMBODIMENTS

Figure 1:
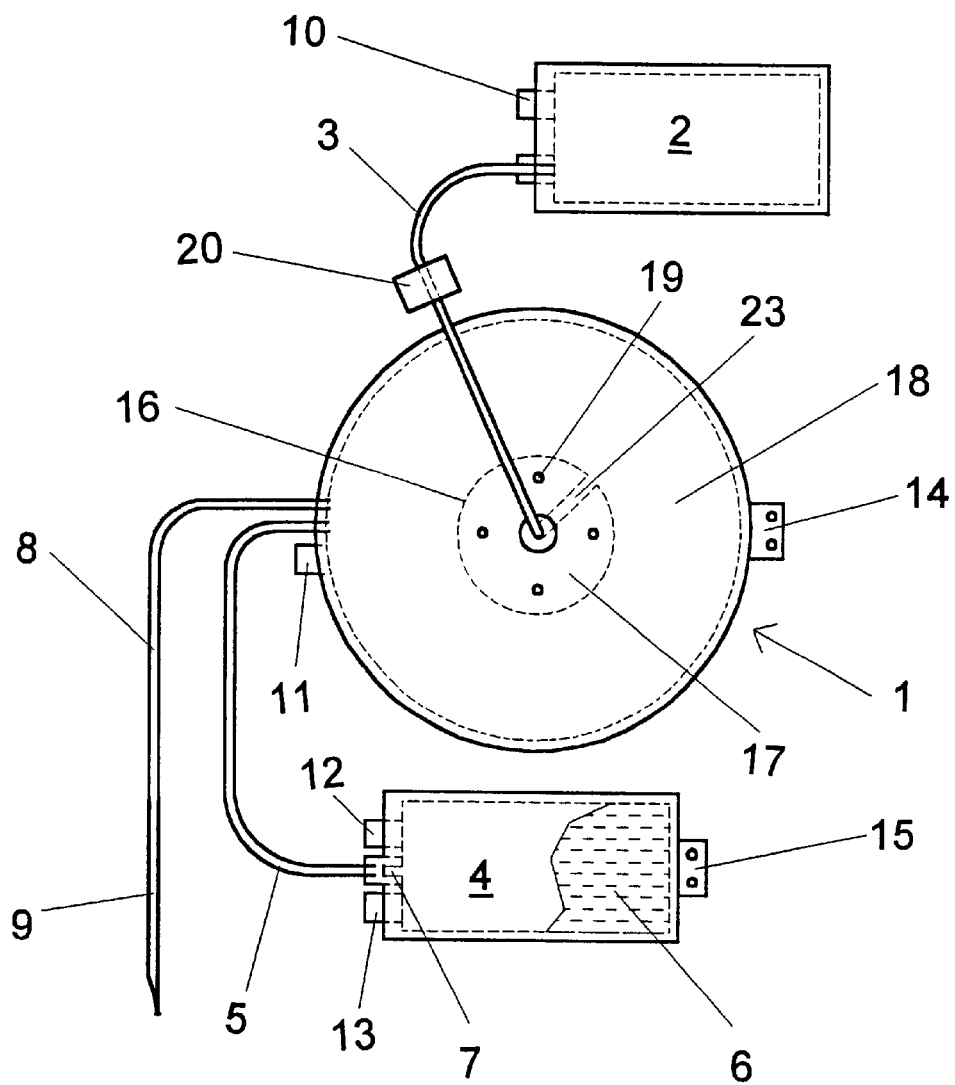
FIG. 1 is a top plan view of an embodiment of a separation set according to the invention. A detachable pinch valve included in the set has been indicated by dashed lines.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

In the first place the separation set is intended for separation of whole blood into the fractions plasma, buffy coat and red blood cells, but it is also suited for separation of other cell suspensions into three fractions when it is essential for the process to be carried out in a closed sterile system and for the fractions to be isolatable in separate containers without opening the system.

The separation container according to FIGS. 1–2 and 4–5 consists of a plate-like separation container 1 of a flexible plastic material, for instance, of the same type as used in conventional blood bags. The separation container can be made, for instance, of two plastic sheetings arranged above each other, which are joined by an annular weld. A first component container 2 is by means of a tube 3 connected to the center of the separation container. A second component container 4 is by means of a tube 5 connected to the separation container in its outer section, preferably at its circumference as shown in the Figure. The component containers can be rectangular bags of a flexible plastic sheeting of conventional type, the plastic sheeting material being selected with regard to the type of cells that are to be stored in the container. In the separation of whole blood, the second component container 4 is initially filled with a certain amount of storage liquid 8 for red blood cells, e.g. SAG solution or SAGMAN solution. Use is normally made of about 63 ml of such a solution for the red blood cells from a blood donation. The component container 4 is in this case temporarily sealed by, for instance, a so-called breaking pin 7. In the embodiment illustrated, the separation container is also provided with a blood withdrawal tube 8 with a withdrawal cannula 9, blood being donated directly from a blood donor to the separation container. The different containers may also be provided with filling and withdrawal ports 10, 11, 12 and 13 of the type that is frequently used on blood bags. The separation container is provided with a suspension device 14 which is arranged in the circumference diametrically opposite to the connection of the tube 5. The component container 4 is provided with a suspension device 15 at its lower edge, i.e. just opposite the edge in which the tube 5 is connected. The separation set further comprises a detachable annular pinch valve 16 (FIGS. 2 and 5) which is mounted on the central part of the separation container and is adapted to shut off a central section 17 from a surrounding annular outer section 18. The pinch valve comprises two coacting parts 21, 22; 44, 45 which are mounted from either side of the separation container.

In the embodiment shown in FIG. 1, the separation container 1 is formed with a number of holes 19 through the container in the central section. The opposite walls (plastic sheetings) of the container are in some portions welded together, and the holes 19 are formed through these portions. The tube 3 between the separation container 1 and the first component container 2 is provided with a remote-controlled pinch valve 20 which is applied directly to the tube. The annular pinch valve (FIG. 2) consists of two disks 21 and 22 which are provided with coupling elements 24, by means of which the disks can be interconnected adjacent to each other so as to define a certain space 25 between themselves. Preferably, the disks are slightly cupped and the coupling elements are arranged on the concave side of each disk. The disks are attached to each other from either side of the separation container 1 with the coupling elements 24 extending through the holes 19. The space 25 between the disks can be adapted to accommodate the volume of buffy coat obtained from a separated blood donation. The upper disk 21 has a groove-shaped opening 23 (FIG. 1) which extends from the circumference to the center and into which the tube 3 is inserted in connection with the mounting. The disks have a slightly angled edge portion 26 along the circumference, which results in an essentially V-shaped groove 27 forming between the disks. A pretensioned elastic ring 28 is arranged in this groove. The ring 28 presses the separation container 1 against the disk 22 such that an annular pinch valve function is achieved. In centrifugation above a certain rotational speed, the elastic ring 28 expands outwards such that the valve opens. The ring 28 can be made of e.g. a rubber material.

Figure 3:
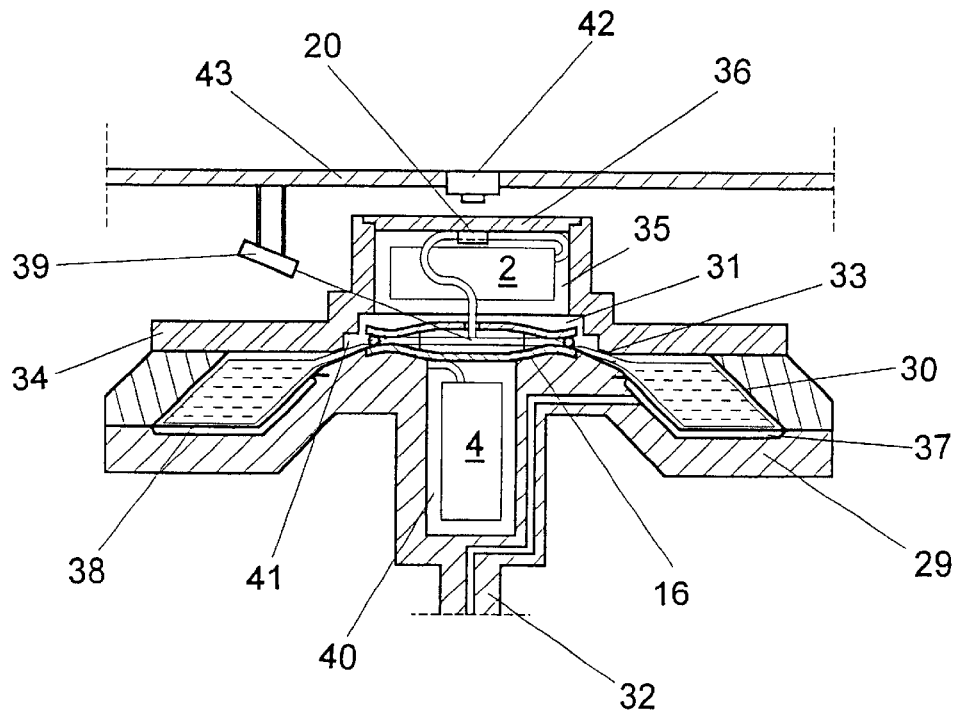
FIG. 3 is a section of a centrifuge rotor, in which a set according to FIGS. 1–2 is mounted.

FIG. 3 illustrates the separation set arranged in a centrifuge rotor 29. The rotor is of a type whose separation space comprises an annular separation compartment 30 and a central compartment 31, which are arranged concentrically with the rotary shaft 32 of the rotor and communicate with each other through a slot-like zone 33. Moreover the rotor comprises means for reducing the volume of the separation compartment during rotation in order to displace a separated fraction from the separation compartment into the central compartment In the embodiment illustrated, the volume of the separation compartment is reduced by pumping hydraulic fluid through a duct in the rotor shaft to an annular hydraulic chamber 37 which is delimited from the separation compartment by means of a flexible diaphragm 38. The separation space is covered with a removable rotor cover 34. Centrally in the rotor cover there is a space 35 where the component container 2 (plasma container) is placed. When the rotor cover is mounted, the space can be reached via a lid 36 in the cover. In the embodiment shown, there is also an elongate narrow space 40 in the rotor shaft below the central compartment The second component container 4 can be placed in this space during centrifugation. In the rotor cover there is also a groove 41 which receives the elastic ring 28 when it expands from its valve-closing position. The rotor cover is suitably made of a transparent material to make it possible to monitor the movement of the separated layers by means of photocells 39 which are mounted in the surrounding casing 43. The remote-controlled tube valve 20 is controlled by the control unit 42 which is correspondingly mounted in the casing. The control unit 42 may consist of an electromagnet that switches the tube valve 20 to its closed position.

The function of the separation set will be described below, the use for separating a blood donation which is donated directly to the separation container 1 being taken as an example. Before the donation, the annular pinch valve 16 has been mounted on the separation container 1, such that it is divided into a central section 17 and an annular outer section 18. Blood is withdrawn from a blood donor through a blood withdrawal tube 8 to the outer section 18. Normally 450 ml of blood are donated. An anticoagulant, for instance CPD solution, is simultaneously supplied or has been supplied in advance to the outer section 18. During donation, the separation set is placed in a blood cradle.

After completion of the donation, the separation set and the connected pinch valve 16 are placed in the centrifuge rotor, such that the central section 17 defined by the pinch valve 16 is positioned in the central compartment 31 and the annular outer section 18 is positioned in the separation compartment 30. The component container 4 is placed in the space 40 in the rotor shaft and the tube 5 is placed in a groove in the rotor. The rotor cover 34 is mounted and the plasma container 2, which is accessible through the lid 36, is fixed to the walls of the cover space 35. The rotor is started and the speed is increased to a predetermined speed of operation. A free filling of the hydraulic chamber 37 can be applied during centrifugation. This means that the space in the separation compartment 30 which is not occupied by the blood quantity is automatically filled by hydraulic fluid being sucked from the hydraulic container (not shown) to the hydraulic chamber 37 by the fact that these communicate with each other as communicating vessels via a by-pass of the hydraulic pump. The blood-filled outer section 18 consequently obtains a somewhat flattened conical shape and its entire radial extent is kept filled with liquid, which results in rapid separation and relatively small interfaces between the separated layers.

The tension in the elastic ring 28 is adapted to resist the centrifugal force up to a certain rotational speed. At higher speeds the centrifugal force surmounts the tension, whereby the ring expands outwards and is caught by the groove 41 in the rotor cover 34. In this connection, the barrier between the central section 17 of the separation container 1 and its outer section 18 opens. The opening and closing of the pinch valve 16 are thus controlled by means of the rotor speed. After a predetermined time the separation is completed. The plasma having the lowest specific weight lies in a circular layer closest to the center, then the buffy coat and furthest away from the center the red blood cells. The by-pass function is now switched off and the hydraulic pump is started. While the rotor spins at a speed which holds the pinch valve 16 open, hydraulic fluid is pumped in under the diaphragm 38. The volume of the separation compartment 30 is reduced and the layers are displaced towards the center. Plasma is displaced through the central section 17 and further through the tube 3 to the plasma container 2. While the plasma fills the plasma container 2, the buffy coat layer moves more and more towards the center of the separation container 1. The movement takes place uniformly from all sides and against the prevailing G field, which makes the buffy coat layer remain intact and mix with the adjoining layers to a minimum extent The movement can be monitored by means of the photocell 39 through the transparent rotor cover, such that the pumping of hydraulic fluid can be stopped when the buffy coat layer is positioned inside the area of the annular pinch valve 16. The control unit 42 now doses the tube valve 20 and the speed of the rotor is reduced such that the tension in the elastic ring 28 surmounts the centrifugal force and returns to the initial position in the V-shaped groove 27. The buffy coat is thus enclosed in the central section 17 of the separation container 1. The centrifuge is braked to come to a stop, the rotor is opened and the separation set is removed.

The plasma container 2 is separated from the separation set by means of a tube welding gun and the rest of the separation set is suspended from the suspension device 15. The breaking pin 7 is broken such that the storage liquid 6 flows through the tube 5 to the separation container and mixes with the red blood cell concentrate. The separation set is then turned and suspended from the suspension device 14, such that the now diluted and somewhat less viscous concentrate of red blood cells flows down into the component container 4. The component container 4 is then separated by the tube 5 being welded together by means of a tube welding gun. The plasma and the red blood cells have thus been isolated in separate component containers. The pinch valve 16 can now be removed and used for a new set of bags. In the separation container 1 remains the buffy coat fraction which can be further processed for recovery of valuable products. For instance, buffy coat fractions from several separations can be combined and centrifuged for recovery of a thrombocyte cell suspension as disclosed in WO 95/01842.

Figure 4:
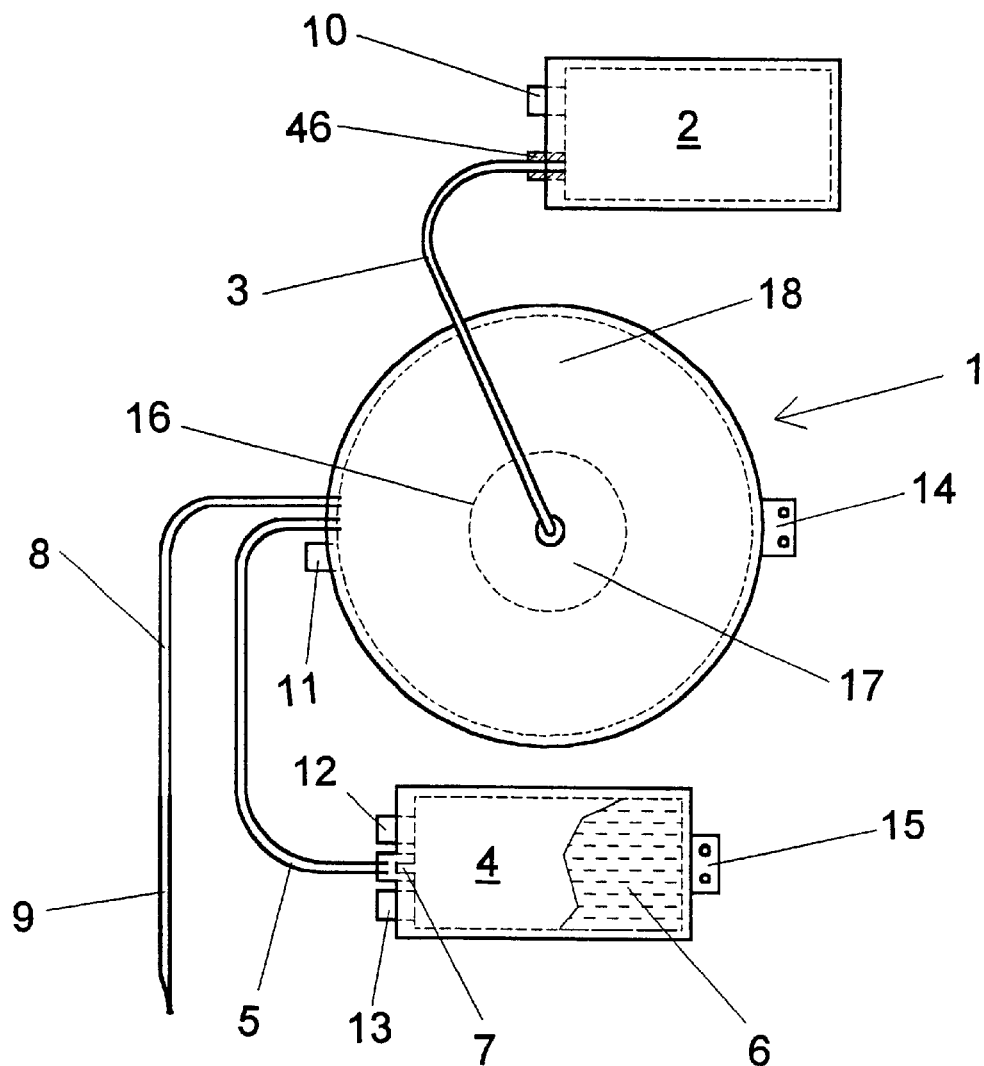
FIG. 4 is a top plan view of another embodiment of a separation set, in which a magnetically acting pinch valve is used. The set is shown without the pinch valve.
Figure 5:
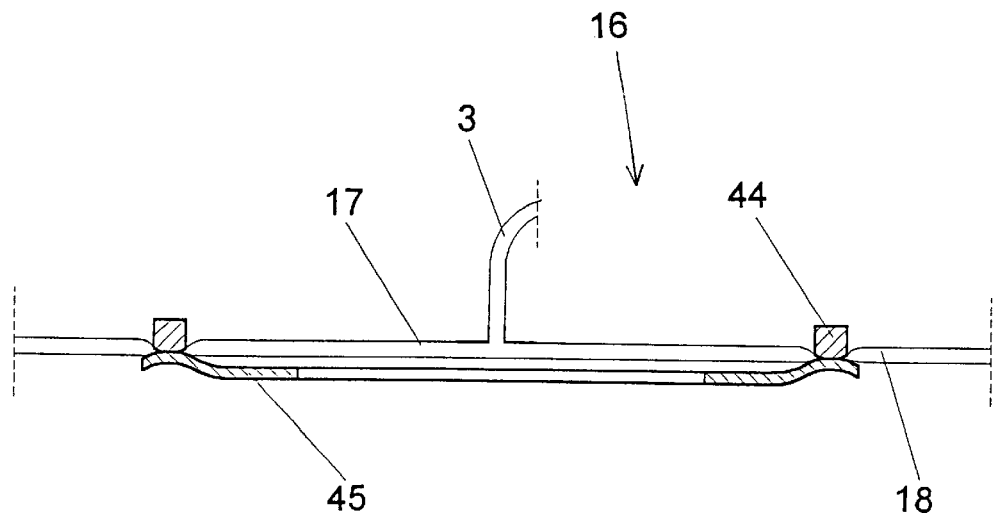
FIG. 5 is a horizontal section of the separation container according to FIG. 4 with the pinch valve mounted

FIGS. 4 and 5 show an alternative embodiment of the set of bags and the pinch valve. FIG. 4 shows the separation container 1 and the associated component containers 2 and 4 and the blood withdrawal tube 8. The pinch valve 16 has only been indicated by a dashed line. Equivalent components in the different Figures have been given the same reference numerals.

Figure 2:
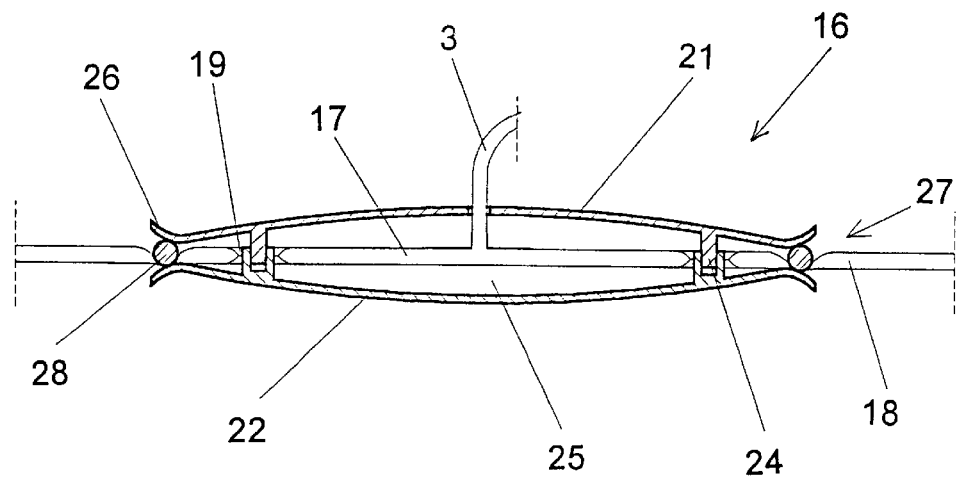
FIG. 2 is. a horizontal section of the plate-like separation container according to FIG. 1 with the pinch valve mounted.

The separation set differs from that described in connection with FIGS. 1 and 2 mainly by the pinch valve 16 consisting of an annular magnet 44 (an annular permanent magnet) and an annular anchor 45 of a magnetically actuatable material, preferably iron sheet. The annular magnet 44 is applied against the upper side of the separation container 1 and the anchor 45 against the opposite side of the container. The annular magnet attracts the anchor and compresses the intermediate container, thereby achieving a valve function. The separation container 1 is thus divided into a central section 17 and a surrounding annular section 18. Holes 19 in the central section 18 are thus not necessary in this embodiment The first component container 2 is provided with a pretensioned non-return valve 46, i.e. the valve requires a certain liquid pressure to open for the liquid to flow into the container and completely blocks the liquid from flowing out The magnetic pinch valve is opened by applying a pump pressure, which is also used to open the valve 46.

Figure 6:
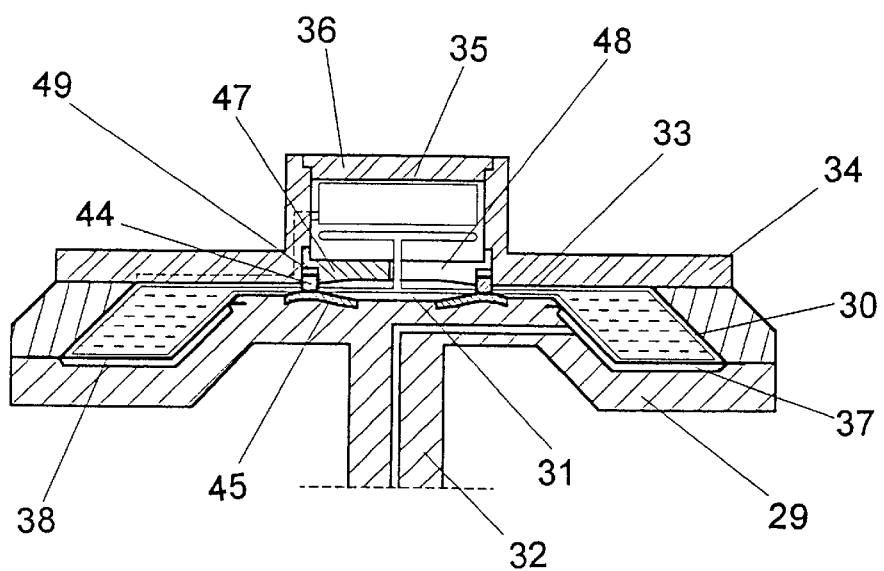
FIG. 6 is a section of a centrifuge rotor, in which the set according to FIGS. 4–5 is mounted.

FIG. 6 illustrates the separation set arranged in a centrifuge rotor 29. The rotor is of a somewhat different type from the one shown in FIG. 3 and does not have, for instance, the elongate narrow space 40 along the rotor shaft. The centrally arranged space 35 in the rotor cover is in this case adapted to hold the two component containers 2 and 4. Equivalent components in the two centrifuges have been given the same reference numerals and are not described in more detail here. Both types of centrifuge can easily be adapted to be used for the two separation sets as described.

Between the central compartment 31 and the space 35 in the cover there is a separate insert 47 which defines these two spaces from each other. The insert 47 has a groove-like opening 48 which extends from its circumference to the center, thereby making it possible to push in the insert between the separation container 1 and the first component container 2, the tube 3 being placed in said groove Furthermore said insert 47 is formed with an annular groove 49 which acts as a guide for the annular magnet 44.

The separation set is placed in the separation compartment of the rotor, such that the central section defined by the pinch valve 16 is positioned in the central compartment 31 and the annular section is positioned in the separation compartment 30. The component containers 2 and 4 are placed in the space 35 in the cover. The rotor is formed with a groove, in which the tube to the second component container is placed.

The separation set functions fundamentally in the same manner as described in connection with FIGS. 1–3. Before donation of blood to the set, the separation container 1 is placed in a fixture (not shown), where the annular magnet 44 and the anchor 45 are mounted in the correct place on the container. The pinch valve now shuts off a central section 17 from an annular outer section 18. Blood is withdrawn from a blood donor through the blood withdrawal tube 8 to the outer section 18 in the same manner as described above.

After completion of the donation, the separation set and the associated pinch valve are placed in the centrifuge rotor. The insert 47 is mounted and the tubes are arranged in grooves intended therefor. The rotor cover 34 is mounted, and the component containers which are accessible through the lid 36 are attached to the walls of the cover space 35. The rotor is then run up to the speed of operation with the by-pass function of the hydraulic pump activated, such that a free filling of the hydraulic chamber occurs in the same manner as described above. The pinch valve 16 is closed while the separation proceeds and the opening and closing thereof are in this case independent of the speed of the rotor.

When the separation is completed, the rotational speed can be reduced to reduce the tension in the cover during the pressing-out of plasma. The by-pass function is shut off and the hydraulic pump is started. A pump pressure forms in the rotor. This pressure increases until the annular magnet 44 comes loose and is pressed upwards to an upper position in the groove 49. The magnetic force decreases rapidly as the gap to the anchor increases, and the groove is made so deep that the magnetic force decreases significantly. The plasma now expands the sheetings in the central compartment 31 and is passed on through the tube 3 to the plasma container 2, where the pretensioned non-return valve opens completely. While plasma fills the plasma container, the buffy coat layer moves more and more towards the center of the separation container as described above. The displacement of the buffy coat layer can be monitored by means of a photocell through the transparent rotor cover, such that the pumping of hydraulic fluid can be interrupted when the buffy coat layer is positioned inside the area of the annular pinch valve. The pumping operation is then interrupted and the by-pass connection is activated, whereby the pressure in the separation container immediately drops. The non-return valve 46 and the annular pinch valve 16 now close. The centrifuge is stopped, the rotor cover is opened and the separation set is removed and then handled in the same manner as described above.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A separation set for blood component preparation to be inserted into a centrifuge rotor having an annular separation compartment and a central component arranged concentrically with an axis of rotation of the rotor and communicating with each other via an annular slot, and having means for reducing a volume of the separation compartment during operation, said separation set comprising:

a plate-like separation container made of a flexible material;

a detachable annular pinch valve mounted on said separation container and dividing said separation container into a central section and an annular outer section;

a first component container connected to a center of said central section by a first tube; and a second component container connected to said outer section by a second tube.

2. The separation set of claim 1, further comprising a blood withdrawal tube which is connected to the outer section of the separation container.

3. The separation set of claim 1, wherein said second tube is connected to the separation container at a circumference thereof.

4. The separation set of claim 1, wherein said central section has portions where opposite walls of the separation container are welded together and in which portions holes are formed through said separation container.

5. The separation set of claim 4, said pinch valve including two disks interconnected from either side of the separation container by coupling elements extending through the holes in the separation container such that a certain space is defined between the disks, said disks having a slightly angled edge portion along a circumference, such that an essentially V-shaped groove is formed between the disks, and further including a pretensioned elastic ring which is arranged in said groove.

6. The separation set of claim 5, wherein said space between the disks is adapted to receive a volume of buffy coat obtained from a separated blood donation.

7. The separation set of claim 1, wherein said pinch valve includes an annular magnet and an annular anchor of a magnetically actuatable material, which are arranged on the separation container from either side thereof.

8. The separation set of claim 1, further comprising a pretensioned non-return valve in the first tube.

9. The separation set of claim 1, wherein said second component container initially contains a storage liquid for red blood cells.

10. The separation set of claim 1, further comprising a suspension device disposed in a circumference of the separation container and arranged diametrically opposite a location where the second tube is connected to the separation container.

11. A blood component separation set for use with a centrifuge rotor and removable as a set therefrom, comprising:

a plate-like separation container made of a flexible material;

an annular pinch valve detachably mounted on said separation container and, when closed, dividing said separation container into a central section and an annular outer section, said central section and said annular outer section being in communication with one another when said pinch valve is opened;

a first component container connected to a center of said central section by a first tube, plasma being displaced to said first component container during centrifugation; and a second component container connected to said outer section by a second tube, red blood cells accumulating in said outer section during centrifugation;

said separation set, after centrifugation, being removed from said centrifuge rotor, said closed pinch valve maintaining separation of said red blood cells for subsequent blood processing outside the centrifuge rotor.

12. The separation set of claim 11, wherein said central section has portions where opposite walls of the separation container are welded together and in which portions holes are formed through said separation container, said pinch valve including two disks interconnected from either side of the separation container by coupling elements extending through the holes in the separation container such that a certain space is defined between the disks, said disks having a slightly angled edge portion along a circumference thereof forming an essentially V-shaped groove between the disks, and further including a pretensioned elastic ring which is arranged in said groove, said pretensioned ring being expanded outward in response to a rotational speed of said centrifuge rotor to allow communication between said central section and said outer section.

13. The separation set of claim 11, wherein said pinch valve includes an annular magnet and an annular anchor of a magnetically actuatable material, which are arranged on the separation container from either side thereof.

14. The separation set of claim 11, further comprising a pretensioned non-return valve in the first tube.

15. The separation set of claim 11, further comprising a blood withdrawal tube connected to the outer section for supplying blood to said separation container.

16. The separation set of claim 11, wherein said second component container initially contains a storage liquid for red blood cells and includes a breaking pin which is broken, after centrifugation, to allow fluid flow into and out of said second component container.

17. The separation set of claim 16, further comprising a suspension device disposed in a circumference of the separation container and arranged diametrically opposite a location where the second tube is connected to the separation container.

18. A blood component separation set for use with a centrifuge rotor and removable as a set therefrom, comprising:

a plate-like separation container made of a flexible material;

an annular pinch valve detachably mounted on said separation container and, when closed, dividing said separation container into a central section and an annular outer section, said central section and said annular outer section being in communication with one another when said pinch valve is opened;

a blood withdrawal tube connected to the outer section for supplying blood to said separation container;

a first component container connected to a center of said central section by a first tube having a pretensioned non-return valve, plasma being displaced to said first component container during centrifugation and prevented from return to said central section by said non-return valve; and a second component container connected to said outer section by a second tube, red blood cells accumulating in said outer section during centrifugation, said second component container initially containing a storage liquid for red blood cells and including a breaking pin which is broken, after centrifugation, to allow fluid flow into and out of said second component container;

said separation set, after centrifugation, being removed from said centrifuge rotor, said closed pinch valve maintaining separation of said red blood cells for subsequent blood processing outside the centrifuge rotor.

19. The separation set of claim 18, wherein said central section has portions where opposite walls of the separation container are welded together and in which portions holes are formed through said separation container, said pinch valve including two disks interconnected from either side of the separation container by coupling elements extending through the holes in the separation container such that a certain space is defined between the disks, said disks having a slightly angled edge portion along a circumference thereof forming an essentially V-shaped groove between the disks, and further including a pretensioned elastic ring which is arranged in said groove, said pretensioned ring being expanded outward in response to a rotational speed of said centrifuge rotor to allow communication between said central section and said outer section.

20. The separation set of claim 18, wherein said pinch valve includes an annular magnet and an annular anchor of a magnetically actuatable material, which are arranged on the separation container from either side thereof.

* * * * *